United States Patent [19]
Buechel et al.

[11] Patent Number: 5,702,448
[45] Date of Patent: Dec. 30, 1997

[54] PROSTHESIS WITH BIOLOGICALLY INERT WEAR RESISTANT SURFACE

[76] Inventors: Frederick F. Buechel, 61 First St., South Orange, N.J. 07079; Michael J. Pappas, 61 Gould Pl., Caldwell, N.J. 07006

[21] Appl. No.: 498,112

[22] Filed: Jul. 5, 1995

Related U.S. Application Data

[63] Continuation of Ser. No. 161,982, Dec. 2, 1993, abandoned, which is a continuation of Ser. No. 882,256, May 13, 1992, abandoned, which is a continuation-in-part of Ser. No. 583,459, Sep. 17, 1990, abandoned.

[51] Int. Cl.⁶ ............................................. A61F 2/28
[52] U.S. Cl. ................... 623/16; 623/18; 623/23; 606/65; 606/69; 606/76
[58] Field of Search .................. 623/11, 12, 16, 623/18, 20, 22, 23, 66; 606/60, 65, 69, 76

[56] References Cited

U.S. PATENT DOCUMENTS

| | | | |
|---|---|---|---|
| Re. 32,449 | 6/1987 | Claussen et al. | 623/22 |
| 3,643,658 | 2/1972 | Steinemenan | 623/16 |
| 3,707,006 | 12/1972 | Bokros et al. | 623/16 |
| 4,040,129 | 8/1977 | Steinemann et al. | 623/18 |
| 4,145,764 | 3/1979 | Suzuki et al. | 623/16 |
| 4,159,358 | 6/1979 | Hench et al. | 623/16 |
| 4,223,412 | 9/1980 | Aoyagi et al. | 623/18 |
| 4,483,678 | 11/1984 | Nishio et al. | 623/16 |
| 4,687,487 | 8/1987 | Hintermann | 623/18 |
| 5,037,438 | 8/1991 | Davidson | 623/18 |
| 5,123,924 | 6/1992 | Sioshansi et al. | 623/16 |

FOREIGN PATENT DOCUMENTS

| | | |
|---|---|---|
| 2 576 793 | 1/1985 | France . |
| 37 22 410.7 | 3/1988 | Germany . |

*Primary Examiner*—David Isabella
*Attorney, Agent, or Firm*—Anthony J. Casella; Gerald E. Hespos; Ludomir A. Budzyn

[57] ABSTRACT

A prosthesis is provided having at least a smooth non-articulating load bearing surface disposed adjacent a bone. The prosthesis includes a substrate formed from a metallic alloy. At least the regions of the substrate defining the load bearing surface are coated with a biologically inert abrasion resistant material harder than the substrate for preventing leaching of ions from the substrate into adjacent body tissue and for preventing wear. The coating may be titanium nitride or zirconium or other such material exhibiting biological inertness and acceptable hardness. The coating preferably defines a thickness of 8–10 microns.

21 Claims, 2 Drawing Sheets

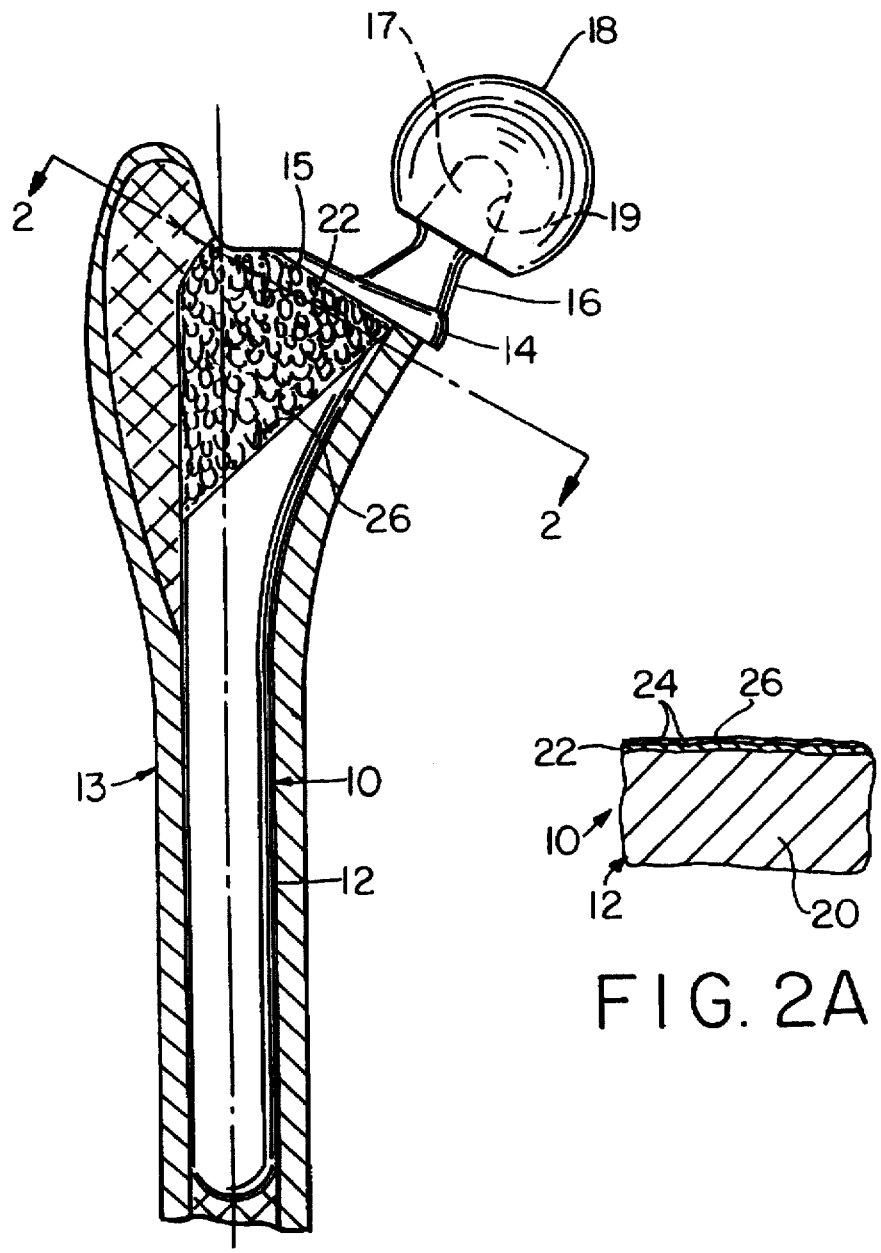
FIG. 1
FIG. 2A
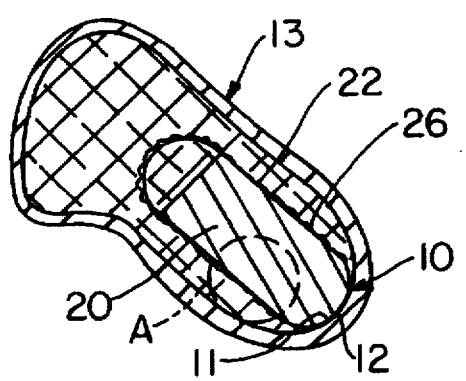
FIG. 2

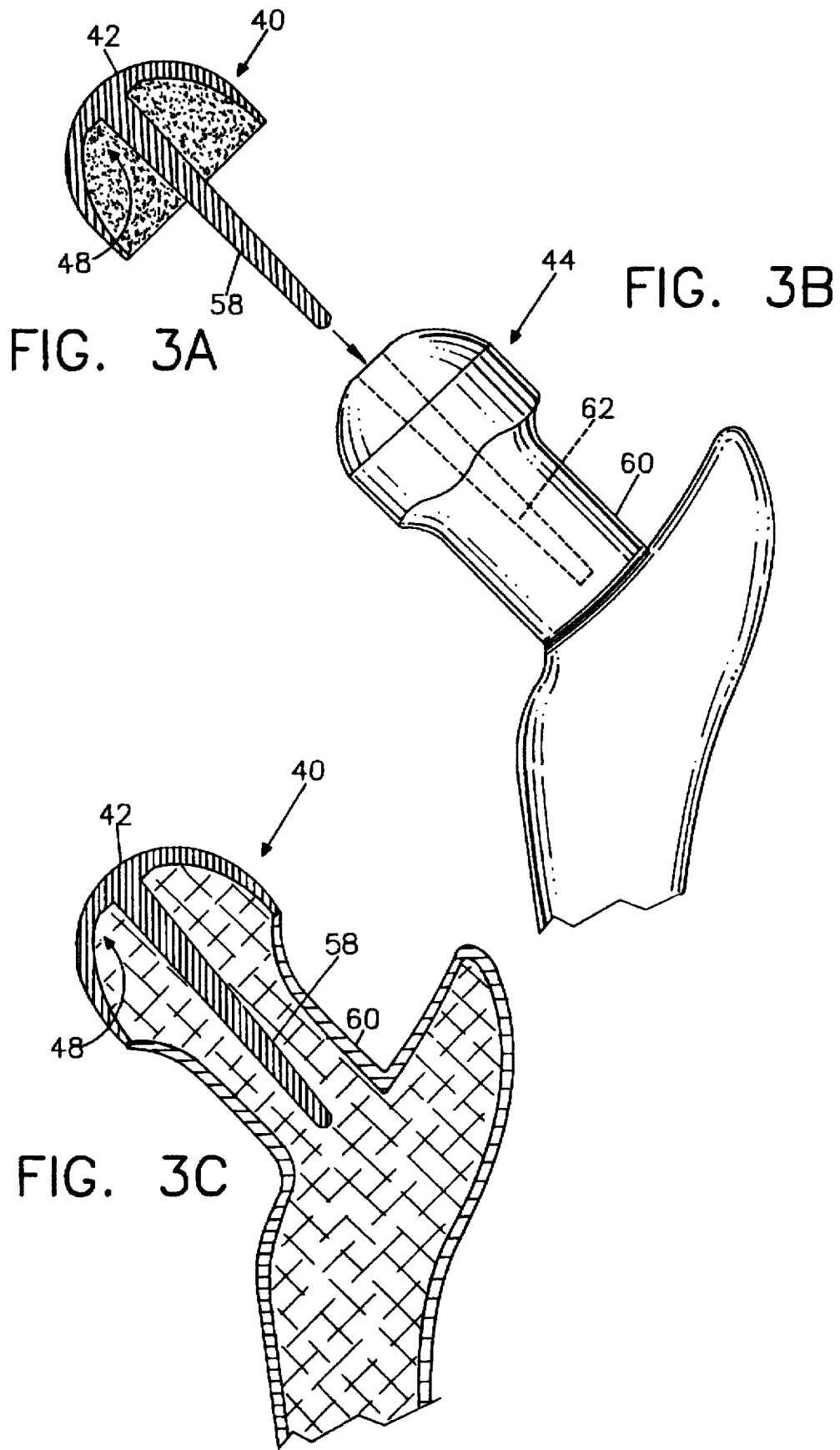

PROSTHESIS WITH BIOLOGICALLY INERT WEAR RESISTANT SURFACE

RELATED APPLICATIONS

This application is a continuation of Ser. No. 08/161,982, filed on Dec. 02, 1993, now abandoned, which is a continuation of application Ser. No. 07/882,256, filed on May 13, 1992, now abandoned, which is a continuation-in-part of application Ser. No. 07/583,459, filed on Sep. 17, 1990, now abandoned.

BACKGROUND OF THE INVENTION

Prior art orthopedic prostheses are used to replace or supplement a portion of the natural bone. Most orthopedic prostheses include at least one surface region intended for secure fixation to the natural bone. Orthopedic prostheses may also include a load bearing surface region that is disposed adjacent to the bone without secure affixation. Many orthopedic prostheses replace a natural joint, such as a knee, hip, shoulder, finger or ankle. Prosthetic joint replacement systems will include two prosthetic components affixed to separate bones and capable of articulating relative to one another. Thus, a component of a prosthetic joint may include an articulating surface region, a load bearing non-articulating surface region and a surface region for direct affixation to adjacent bone.

Prior art prosthetic systems have employed screws, wedge fitting and cement either separately or in various combinations to fix the prosthetic device to the bone. However, cement is known to at least partly deteriorate after an extended time in the body, thereby causing a shifting of the prior art prosthetic device relative to the bone. This movement abrades the cement, the bone and the prosthetic device, resulting in release of wear debris which produces bone death and further loosening. Prosthetic devices relying entirely on screws or wedge fitting also may shift over time in response to changes in the natural bone and/or forces exerted on the prosthesis, and abrasion resulting from such shifting generates wear debris as explained above.

The more recent prior art has included prosthetic devices with surface coatings or modifications that are intended to enhance natural bone ingrowth to the prosthesis for achieving a biological fixation of the prosthesis to the natural bone. More particularly, at least selected surface areas of these prior art prostheses are provided with a macro surface defining pores, fissures, texturing or the like into which the natural bone tissue may grow. This biological fixation is intended to stabilize the prosthetic device relative to the bone and substantially prevent the loosening or shifting which had occurred with the above described earlier fixation means.

The surface treatment to enhance the bone ingrowth to the prior art prosthetic device can be achieved in many ways. A common surface treatment for prior art prosthetic devices is referred to as a porous coating which is applied to the metallic substrate of the prosthesis to define an array of small pores or fissures in the surface of the prosthesis. Other prior art prosthetic systems apply a metallic mesh material to a substrate, such that the mesh material defines the texture into which bone tissue may grow. Still other prior art systems directly modify the substrate to define the surface irregularities, such as small holes, fissures, slots or the like.

Orthopedic prosthetic devices typically are formed from a metallic alloy that will exhibit appropriate strength and flexure in use. Examples of metallic alloys that are currently used for orthopedic prosthetic devices include titanium alloys, such as a titanium aluminum vanadium alloy, and cobalt-chromium alloys, such as a cobalt-chromium molybdenum alloy. Although both titanium and cobalt-chromium alloys exhibit appropriate strength and flexure for most applications, each such alloy has its own unique advantages and deficiencies. For example, cobalt-chromium exhibits desireable hardness, and hence is widely used for prosthetic devices having an articulating surface region. However, cobalt-chromium is very expensive and its desireable hardness characteristics make it difficult to machine. Furthermore, some patients exhibit sensitivity to cobalt-chromium alloys. Additionally, some cobalt-chromium alloys are known to release metallic ions as a result of corrosion after extended exposure to the biological tissue of the human body. These ions are suspected to cause tumors and may have carcinogenic effects.

The amount of ion released from the alloys defining the substrate of prosthetic devices generally has been considered acceptably low. However, it is known that the amount of ion release increases with the surface area of the prosthesis. The relatively recent advent of surface coatings or modifications to promote bone ingrowth results in a very substantial increase in surface area. More particularly, pores, fissures or other such surface irregularities vastly increase the surface area for a given prosthesis as compared to the same prosthesis having a smooth exterior surface. This increase in surface area achieved by the pores, texturing or other surface irregularities has resulted in an increase in the ion release from the alloy from which the prosthesis is made. The ions released from the alloy of the prior art prosthetic device may leach into the body and migrate to areas remote from the prosthetic device. Patients having prostheses with surface treatments for promoting bone ingrowth have been observed to have ions in urine specimens, liver tissue, and other body locations remote from the prosthesis.

In view of these fairly recent findings, some doctors recommend not employing prostheses with macro surface treatments in young patients who may be expected to be exposed to the large surface area of ion releasing alloys for a number of years and who therefor run a greater risk of being adversely impacted by the tumor causing or carcinogenic effects of the ions.

In addition to the preceding negative effects of ion release from prior art prosthesis having surface treatments for promoting bone ingrowth there is a desire to improve the biological fixation between the prosthesis and the natural bone. The ingrowth of bone to the macro surface region of the prior art prosthesis often is not complete. Data suggest that bone will grow into only about 10–20% of many prior art macro surface area. Furthermore, a thin fiber layer may exist between the substantially rigid bone and the pores, fissures or other irregularities of some the prior art macro surfaces. This relatively incomplete bone ingrowth may be due to the above described corrosion reaction and resulting ion release. The effect of the incomplete bone ingrowth may be some movement between the prosthesis and the bone. As noted above, such movement will generate metallic wear debris. The small metallic particles produced by such wear corrode rapidly in view of the relatively large surface area to volume ratio for these particles. As noted above, corrosion results in the undesirable metallic ion release. Thus a more complete biological fixation could reduce the potentially harmful metallic ion release.

Titanium alloy prostheses generally are considered to be much more biologically compatible than the cobalt-chromium alloys. Thus, the sensitivity some patients have to cobalt-chromium prostheses generally is not a problem for titanium alloy prosthetic components. Titanium alloys also are substantially less expensive than cobalt-chromium alloys, but they are not as hard. Thus, titanium alloys prosthetic components are likely to generate wear debris when employed on articulating surface regions of a prosthetic component or on a non-articulating load bearing surface region that is subject to micromovement relative to adjacent bone. The metallic wear debris particles cause further deterioration of both the prosthetic component and the natural bone.

The prior art has included prosthetic components formed from a plurality of different metallic alloys. For example, femoral prosthesis have been provided with a titanium alloy stem and neck and a cobalt-chromium alloy head. The comparatively harder cobalt-chromium head performs well as an articulating surface. The titanium alloy stem and neck achieve better biocompatibility at a lower cost. However, galvanic action is known to be generated at the interface of the titanium alloy neck and the cobalt-chromium alloy head, with a corresponding corrosion and generation of corrosion-related debris. Additionally, load bearing areas of the stem are subject to micromovement relative to the bone, and hence these areas can generate significant wear debris. Furthermore, it would be desireable to provide a less expensive, harder and more biologically compatible head than the cobalt-chromium head in the prior art system.

The prior art also has included attempts to provide coatings on a metallic alloy prosthesis to enhance some aspect of its performance. The coatings have included ceramics which are noted for their hardness and their biological compatibility. These ceramic coatings have been applied to the metallic alloy substrate by known thin film technology. This technology is widely used, for example, in the machine tool arts to enhance the life of cutting tools. Prior art thin film technology typically applies the ceramic coating to a substrate in a vacuum coating chamber. The substrate to be coated functions as the cathode in the chamber, while the anode is formed from the material to be coated onto the substrate. An arc is struck in the chamber, and the substrate to be coated is subjected to high energy ion bombardment from the anode. A gas is then introduced into the chamber. The gas reacts with the ions of the anode and produces an ionic deposition of a highly-adherent ceramic coating onto the substrate. This thin film technology typically is employed to provide an ionically bonded coating approximately 2–4 microns thick. Thicker ceramic coatings have been considered too costly and problematic for application by thin film technology, and hence thin film technology has not been employed for thicker coatings in the machine tool art and have not been carried over into the orthopedic prosthetic art. The problems of using thin film technology to produce a thick coating have been cracking and eventual delamination. It has been believed that cracking occurs in part due to the different stiffnesses of the metallic alloy substrate and the ceramic coating. Thus, ceramic coatings applied by thin film technology on prosthetic devices generally have been in the range of 2–4 microns thick on articulating surfaces to avoid delamination and to minimize coating costs. Ceramic coatings applied by thin film technology to non-articulating surfaces are intended primarily to achieve biological compatibility, and hence have been at the lower end of this 2–4 micron range of coating thicknesses. Ceramic coatings have been applied to greater thickness by other coating technologies (e.g. plasma spray) primarily for other art areas, such as kitchen appliances. However, thick ceramic coatings applied by other technologies are also subject to cracking and delamination.

Despite the known hardness and wear resistance of thin film ceramic materials, the inventors herein have determined that thin film ceramic coatings applied to articulating surfaces tend to wear through well within the anticipated life of the patient and the prostheses. The wearing through of the prior art ceramic coating exposes the prior art metallic alloy substrate with the above described problems of wear debris, corrosion and biological incompatibility. The inventor's herein further believe that similar wear through occurs at other load bearing non-articulating surfaces due to the above described micromovement between the coated prosthesis and adjacent bone.

In view of the above, it is an object of the subject invention to provide an orthopedic prosthesis with enhanced wear resistance.

It is another object of the subject invention to provide an orthopedic prosthesis that ensures both wear resistance and biological compatibility.

A further object of the subject invention is to provide an orthopedic prosthesis that avoids galvanic corrosion between dissimilar metallic alloys of a prosthetic system.

Yet another object of the subject invention is to provide a coated orthopedic prosthesis that avoids cracking and delamination in use.

SUMMARY OF THE INVENTION

The subject invention is directed to an orthopedic prosthesis. The prosthesis of the subject invention comprises a substrate formed from a metallic alloy selected to exhibit appropriate strength, flexibility and weight characteristics. Examples of such alloys may include a titanium alloy, such as a titanium aluminum vanadium alloy, or a cobalt-chromium alloy, such as a cobalt-chromium molybdenum alloy.

The orthopedic prosthesis of the subject invention includes at least one load bearing surface for transferring an applied load to the natural bone. At least selected portions of the surface of the prosthesis may be coated or modified to enhance bone ingrowth and hence achieve biological fixation to the bone in which the prosthetic device is implanted. More particularly, at least selected surface areas may be appropriately treated to define surface irregularities or texturing. The surface irregularities may be in the form of pores, fissures, holes, slots or the like defining small regions into which bone tissue may grow for achieving a biological fixation of the prosthetic device to the bone. The surface treatment may be defined by a coating applied to the prosthesis or by appropriate modification of the substrate of the prosthesis. The pores, fissures or other such surface irregularities each preferably are in the range of 150–500 microns across. However, at least selected load bearing surfaces of the prosthesis may be smooth to prevent bone ingrowth. The prosthesis may further include an articulating surface region for articulation relative to another component in a prosthetic system.

The prosthesis of the subject invention further comprises a coating of a material that is harder and more abrasion resistant than the metallic alloy substrate of the prosthesis. The coating is applied by thin film coating technology to achieve ionic bonding at least to areas of the prosthesis that are subject to movement relative to an adjacent surface. For example, the coating may be applied to a relatively smooth load bearing surface of the prosthesis that is subject to micromovement relative to adjacent surfaces of the bone. The hard abrasion resistant coating may also be applied to articulating surfaces of the prosthesis.

The hard abrasion resistant coating also preferably is biologically inert and may be applied to areas of the prosthesis having the surface treatment for promoting bone ingrowth. The relatively inert coating is applied in a manner to maintain the overall surface irregularities on the prosthesis for promoting bone ingrowth. Furthermore, the coating is applied with a thickness that will keep the surface irregularities in the above described range of 150–500 microns for optimizing bone ingrowth. Thus, the surface regions of the prothesis that are treated to achieve bone ingrowth are sealed to prevent ion release and leaching despite the substantial increase in surface area for these regions of the prosthesis.

A preferred hard biologically inert coating material, as explained further below, is titanium nitride. Alternate coating materials are zirconium, titanium boride, titanium carbide, aluminum oxide and diamond. These materials have been demonstrated to be substantially completely biologically inert even when exposed for extended periods of time and even with the very large surface areas inherent in regions of the prothesis that are treated as described above for promoting bone ingrowth. Furthermore, these coating materials exhibit desirable hardness characteristics for preventing or reducing wear of the prosthesis and corresponding generation of microscopic wear debris particles. Wear debris that may be generated will be biologically inert. Other coating materials exhibiting such biological inertness and desirable hardness and wear characteristics may also be employed.

In addition to preventing the leaching of ions from the substrate alloy of the prosthesis, the coating will significantly improve the biological fixation of some substrates. More particularly, the improved biological compatibility and the enhanced hardness and wear characteristics achieved by the subject coating will define an environment that is more conducive to bone ingrowth and hence a superior biological fixation.

The hard, abrasion resistant biologically inert coating preferably is applied to a thickness of 5–15 microns, and more preferably in the range of 8–10 microns. It has been found that ceramic coatings with thicknesses in the above stated range and applied by thin film technology perform without the cracking or delamination that had been observed with thicker coatings employed on machine tools. Furthermore, as explained below, tests have shown that articulating surfaces with coatings having thicknesses in the above stated range remain intact and substantially free of damage and wear debris for more than 25 million cycles in a test machine that accurately simulates an articulating prosthetic joint. In contrast, a prosthetic device having the prior art coating thickness of 2–4 microns displayed at least localized wear through of the coating to the substrate after only 7–8 million cycles. The virtual absence of wear and related debris on the prosthetic device coated to a thickness in the above stated range is believed to be attributable to the greater coating hardness that is achieved with thin film technology after extended ionic bombardment in the vacuum coating chamber. Additionally, it is believed that the greater thickness gives a more crystalline structure to the ceramic coating as opposed to an amorphous structure existing with the 2–4 micron prior art coating or with coatings applied by other coating technologies. This crystalline structure achieved with the thicker coating provides unexpectedly greater hardness and superior abrasion resistance. Thus, the subject invention enables more efficient and effective prosthetic systems.

BRIEF DESCRIPTION OF THE DRAWINGS

FIG. 1 is a front elevational view of a prosthesis in accordance with the subject invention.

FIG. 2 is a cross-sectional view taken along line 2—2 in FIG. 1.

FIG. 2A is an enlargement of area A in FIG. 2.

FIG. 3A, 3B and 3C are diagrammatical cross-sectional illustrations of a femoral hip surface replacement prosthesis and the resected head of the femur.

DETAILED DESCRIPTION OF THE PREFERRED EMBODIMENT

A femoral stem-type prosthesis in accordance with the subject invention is identified generally by the numeral 10 in FIGS. 1, 2 and 2A. It is to be understood that the femoral stem-type prosthesis 10 depicted and described herein is only one example of the many prosthesis that may incorporate the subject invention. The femoral stem-type prosthesis 10 includes an elongated stem 12 for insertion into the intramedullary cavity 11 of the natural femur 13. The prosthesis 10 further includes a collar 14 adjacent the stem 12 and extending outwardly in anterior, posterior and medial directions therefrom. More particularly, the collar is angularly aligned and dimensioned to be in face-to-face contact with a proximal end 15 of the natural femur 13 for delivering loads thereto. A neck 16 extends from the collar 14 and terminates at a frustoconical mounting end 17. A spherical head 18 is provided with a frustoconical mounting cavity 19 into which the mounting end 17 of the neck 16 is fit. The spherical head 18 will define an articulating surface relative to a plastic bearing liner of an acetabular prosthetic component (not shown). Thus, the head 18 will be subjected to considerable wear as the prosthesis 10 repeatedly articulates under various applied loads. The smooth surfaces of the stem 12 also are subject to wear in view of repeated micromovement of the stem 12 relative to adjacent regions of the bone 13. As noted above, this wear had produced microscopic debris in prior art prostheses.

The prosthesis 10 includes a metallic alloy substrate 20 formed from a material that will exhibit desirable strength, hardness and flexure characteristics for the particular use of the prosthesis. A preferred alloy for the substrate 20 is a titanium alloy, such as a titanium aluminum vanadium alloy. Titanium alloys are less expensive than many other optional alloys, are relatively easy to machine and exhibit exceptional biological compatibility. Cobalt-chromium alloys, such as a cobalt-chromium molybdenum alloy may also be used as a coated or uncoated substrate 20 for at least part of the prosthesis 10. Cobalt-chromium alloys generally cost more than titanium alloys and are less biologically compatible. However, some physicians prefer cobalt-chromium for at least portions of the prosthesis 10 in view of its hardness. For example, a titanium alloy may be used as the substrate 20 for the stem 12, collar 14 and neck 16. A cobalt-chromium alloy may be used for the head 18. Other alloys selected by the physician for exhibiting appropriate strength, flexure and hardness characteristics may also be used for the substrate 20.

A proximal portion of the stem 12 of the prosthesis 10 is provided with a porous coating 22 for promoting bone ingrowth and achieving biological fixation with the bone 13 into which the prosthesis 10 is implanted. The porous coating 22 preferably defines a continuous array of pores 24 as shown in FIG. 2A having cross-sectional dimensions of between 150–500 microns each, and preferably 300–350 microns, with a preferred average pore size of about 325 microns. The porous coating 22 may be the same alloy as the substrate 20 of the prosthesis 10 but separately applied thereto. In other embodiments the macro surface treatment 22 on the prosthesis 10 may be defined by a mesh defining a textured or otherwise irregular surface area that will promote bone ingrowth. In still other embodiments the modified surface area 22 may be a knurling unitary with the substrate 20. The particular location of the surface coating or modification 22 on the stem 12 is described in greater detail in U.S. Pat. No. 4,904,263 which issued to the inventors herein on Feb. 27, 1990. However, other locations for the surface coating or modification 22 may be provided, particularly with other protheses.

As shown most clearly in FIG. 2A, the prosthesis 10 further includes a hard, wear resistant, biologically inert coating 26 applied by thin film coating methods uniformly over at least selected surface areas of the substrate 20 including at least selected surface areas that are subject to wear. In particular, the hard wear resistant coating material 26 preferably is applied to the smooth surface areas of the stem 12 that are subject to micromovement relative to the bone and/or to the outer spherical articulating surface of the head 18. The porous coating 22 or other such surface modification of the substrate 20 for promoting bone ingrowth and biological fixation may also be coated. The inert coating material 26 extends into the pores 24 defined by the porous coating 22 such that the contact area between biological tissue and the porous coating 22 of the prosthesis 10 is substantially reduced by the inert coating 26. Thus, the leaching of ions from either the substrate 20 or the porous coating 22 can be substantially reduced by the inert coating 26 which covers all or substantial portions of the surface area of both the substrate 20 and the porous coating 22.

The hard wear resistant inert coating 26 also preferably is applied to the frustoconical end 17 of the neck 16, particularly for embodiment of the prosthesis employing a titanium alloy substrate for the stem 12 and neck 16 and employing a cobalt-chromium alloy for the head 18. In these latter embodiments, the frustoconical cavity 19 extending into the spherical head 18 need not be coated. The hard, wear resistant inert coating 26 applied to the frustoconical end 17 of the neck 16 achieves several objectives for this embodiment. First, the galvanic corrosion caused by the interaction between abutting surfaces of the titanium alloy neck and the cobalt-chrome alloy head is entirely avoided by the inert coating material 26 therebetween. Furthermore, the hard wear resistant characteristics of the coating material 26 substantially prevent the generation of any wear debris that could otherwise be caused by micromovement between the end 17 of the neck 16 and the spherical head 18. This enables physicians to employ the hard cobalt-chromium head 18 with the less expensive titanium alloy neck 16 and stem 12 without the penalty of galvanic corrosion and wear debris.

The inert coating 26 is formed from a material that is harder than the substrate 20. The hard, wear resistant, inert coating 26 preferably is titanium nitride or zirconium oxide, and most preferably titanium nitride in view of its effectiveness at an acceptable cost. Other biologically inert materials that are now known or that may be developed may similarly be applied for the purposes explained herein. The inert coating 26 defines a thickness of 5–15 microns, and preferably approximately 8–10 microns. As noted above, it has been determined that the production of a coating by thin film coating technology to achieve a thickness of 8–10 microns results in the ionically bonded coating being harder than a coating of identical materials applied to the traditional 2–4 micron thickness employed in the prior art. The heat and additional ion bombardment to achieve this greater thickness by thin film coating technology is believed to contribute to a substantially greater hardness. Additionally, the thicker coating 26 is believed to exhibit a more pronounced crystalline structure which is harder than the more amorphous structure for thinner applications of the coating 26. This thickness also ensures that the size of the pores 24 remains within the range found to be most acceptable for promoting bone ingrowth.

The titanium nitride preferred for the coating 26, and the other optional inert coating materials identified above, are known to exhibit superior hardness, scratch resistance and lubricity. The hardness of titanium nitride and other such coatings 26 enables nonporous articulating surface areas of the head 18 of the prosthesis and the non-articulating load bearing surfaces subject to micromovement to be polished to achieve a substantially smoother surface than can be achieved with softer materials. More particularly, the articulating surfaces and at least certain non-articulating load bearing surfaces subject to micromovement relative to the bone are polished to approximately 1.0 microinch roughness or less. This contrasts to prior art prostheses which have been polished only to about 4.0 microinch roughness. The much smoother characteristics of surfaces subjected to wear that are enabled by the harder coating 26 contribute substantially to wear resistance, abrasion resistance and lubricity. The hard smooth surface achieved by the coating 26 on the head 18 substantially minimizes the generation of metallic wear debris that could otherwise result from the metal/plastic articulation resulting from engagement of the head 18 of with an acetabular prosthetic component (not shown). The coating thickness of approximately 8–10 microns on the articulating surface of the head 18 has remained substantially in tact on articulating surfaces after subjection more than 25 million cycles in a test machine where the head 18 of titanium alloy with the coating 26 of titanium nitride is engaged with and articulated against an acetabular prosthetic component having a plastic bearing liner. The more than 25 million cycles without significant damage or wear debris is substantially in excess of the performance enabled by prior art articulating prosthetic joints coated to 4 microns thickness where a wear through of the coating to the substrate was observed after 7–8 million cycles. The superior performance of the thicker coating is believed to be attributable to the greater hardness that is unexpectedly achieved with the thicker coatings applied by thin film coating techniques as explained herein. Additionally, none of the purported problems of cracking and delamination reported in the machine tool art were observed after 25 million cycles on the prostheses with the 8–10 micron thick coating.

The inert coating 26 is applied after fabrication, polishing and preliminary cleaning, by initially fixing the prosthesis 10 on a rotating mount in a vacuum coating chamber. Following evacuation of the chamber, ionic surface cleaning is achieved by striking an arc and producing a highly ionized titanium plasma. The prosthesis 10 are given high negative charge which attracts the plasma and subjects the prosthesis 10 to a high energy titanium ion bombardment. In addition to ionic surface cleaning, this also deposits a thin titanium film on the prosthesis 10 and heats them to the requisite temperature for TiN coating. When a titanium alloy prosthesis is coated, this thin titanium film is integrated into the titanium substrate 20. On other materials this film is ionically bonded to the substrate 20 and protects the prosthesis 10 against surface corrosion. Nitrogen gas at low partial pressures is then introduced into the chamber. This gas reacts with the titanium plasma and produces the ionic deposition of a highly-adherent ceramic TiN coating 26 about 8–10 microns in thickness.

An alternate embodiment of the prosthesis is illustrated in FIGS. 3A–3C. More particularly, a hip surface prosthesis is identified by the numeral 40 in FIGS. 3A–3C and includes a highly polished spherical outer load receiving surface 42 and a porous coated interior primary surface 48 having a longitudinally extending stem 58 projecting centrally from the interior of the prosthesis 40. The prosthesis 40 is for being implanted in the resected head 44 of the femur 46 with the stem 58 being driven into a prepared hole 62 formed in the neck 60 of the femur 46. The outer applied load receiving surface 42 of the prosthesis 40 is for replacing the articular surface of the head of the natural femur and for receiving the load applied to the prosthesis during articulation. The porous coated interior surface 48 is intended to provide interlocking fixation between the prosthesis 40 and the resected head 44 of the femur 46 by direct bone ingrowth. As explained with the previous embodiment, the porous coating 48 results in a substantial increase in surface area. To prevent an unacceptable ion release from the porous coating 48 and to enhance bone ingrowth, the porous coating 48 is provided with a top inert coating 66 at a thickness of 5–15 microns and preferably about 8–10 microns. The inert coating 66 preferably is titanium nitride, but may be one of the alternate coatings identified above. The inert coating 66 also is preferably applied to the outer applied load receiving surface 42 and to the stem 58. The inert coating 66 applied to the applied load receiving surface 42 is polished to achieve an acceptably high degree of smoothness. The hardness of the inert coating 66 substantially prevents the generation of metallic wear debris that would otherwise result from articulation between the surface 42 and the acetabular component of a prosthetic system. Similarly, the hardness of the inert coating 66 applied to the stem 58 prevents the generation of wear debris that could result from either the initial driving of the stem 58 into the prepared hole 62 in the neck 60 of the femur 46 or from post-operative movement resulting from loads applied to the prosthesis.

While the invention has been described with respect to a preferred embodiment, it is apparent that various changes can be made without departing from the scope of the invention as defined by the appended claims. In particular, the coating may be defined by other biologically inert and sufficiently hard metals or ceramics. The coating may be applied to prosthesis other than the femoral prosthesis depicted in the Figures. The coating may be applied to the entire prosthesis and not only to areas thereof having the bone ingrowth surface modification or coating. The surface treatment to which the coating is applied may be any surface irregularity employed for promoting bone ingrowth and necessarily increasing the surface area of the prosthesis. These and other variations will be apparent to the person skilled in the art.

We claim:

1. An orthopedic prosthesis formed from a metallic alloy and having at least one load bearing surface movably disposed adjacent to an opposed surface and at least one bone ingrowth surface, said prosthesis comprising a substrate formed from at least one selected metallic alloy and an abrasion resistant, biologically inert coating formed from a ceramic material harder than the substrate, said coating being ionically bonded to the substrate forming a unitary layer on portions of the prosthesis defining the load bearing surface and portions of the prosthesis defining the bone ingrowth surface, said coating defining a thickness of 8–10 microns.

2. An orthopedic prosthesis as in claim 1, wherein the coating defines a crystalline structure.

3. An orthopedic prosthesis as in claim 1, wherein at least a portion of the substrate is formed from a titanium alloy, and wherein the ceramic coating comprises titanium.

4. An orthopedic prosthesis as in claim 3, wherein the coating is titanium nitride.

5. An orthopedic prosthesis as in claim 3, wherein at least a portion of the prosthesis is formed from a cobalt-chromium alloy.

6. An orthopedic prosthesis as in claim 5, wherein the portion of the prosthesis comprising the cobalt-chromium alloy is engaged with a portion of the prosthesis having the titanium alloy substrate with the coating thereon.

7. An orthopedic prosthesis as in claim 5, wherein the portion of the prosthesis formed from the cobalt-chromium alloy is not coated with the ceramic material.

8. An orthopedic prosthesis as in claim 1, wherein the load bearing surface comprises a non-articulating substantially smooth load bearing surface disposed for load bearing micromovement adjacent to a bone.

9. An orthopedic prosthesis as in claim 8, wherein the load bearing surface further comprises an articulating surface disposed for load bearing articulation with respect to another prosthetic component.

10. An orthopedic prosthesis as in claim 9, wherein the bone ingrowth surface area comprises a non-smooth surface configuration for increasing surface area and promoting bone ingrowth.

11. An orthopedic prosthesis as in claim 1, wherein the coating formed on the load bearing surface is polished to a smoothness of approximately 1 microinch.

12. A prosthetic device for biological fixation to a bone, said prosthetic device comprising a metallic alloy substrate, a first portion of said substrate defining a bone ingrowth surface area having a non-smooth surface configuration for increasing surface area and promoting bone ingrowth, a smooth articulating surface area spaced from the bone ingrowth surface area and a smooth load bearing surface area spaced from both the bone ingrowth surface area and the articulating surface area, the bone ingrowth surface area, the articulating surface area and the load bearing surface area all being provided with a unitary substantially biologically inert scratch resistant coating exhibiting greater hardness than the metallic alloy substrate for substantially preventing metallic ion release from the substrate and for preventing production of metallic wear debris, said biologically inert scratch resistant coating defining a thickness of 8–10 microns, whereby the coating prevents ion leaching from the substrate into adjacent tissue.

13. A prosthetic device as in claim 12, wherein the prosthetic device is a femoral stem-type prosthetic device having a stem defining a portion of the prosthetic device having said bone ingrowth surface area, a neck extending from said stem and a head having a cavity therein engaging a proximal portion of said neck, the head comprising the articulating surface of the prosthetic device, the proximal portion of the neck having the coating thereon and the cavity in the head being substantially free of the coating.

14. A prosthetic device as in claim 12, wherein the substrate is formed from a titanium aluminum vanadium alloy.

15. A prosthetic device as in claim 12, wherein a portion of the prosthetic device is formed from a cobalt-chromium molybdenum alloy.

16. A prosthetic device as in claim 12, wherein the biologically inert coating is a titanium nitride.

17. A prosthetic device as in claim 12, wherein the biologically inert coating is zirconium oxide.

18. A prosthetic device as in claim 12, wherein the bone ingrowth area is defined by a plurality of pores each of which defines a cross-sectional dimension in the range of 150–500 microns.

19. A prosthetic device as in claim 12, wherein the biologically inert material is selected from the group consisting of titanium nitride, zirconium, titanium boride, titanium carbide, aluminum oxide and diamond.

20. A prosthetic device as in claim 12, wherein the prosthetic device comprises a first component having the smooth load bearing surface thereon and a second component having the smooth articulating surface thereon, the first and second components having engagement surfaces defining an interface therebetween, said first component having the coating on the engagement surface, the second component being substantially free of the coating on the engagement surface thereof.

21. An orthopedic prosthesis comprising at least one substantially smooth non-articulating load bearing surface area for placement in proximity to a bone and at least one substantially smooth articulating load bearing surface area for articulation against another orthopedic prosthetic component, the orthopedic prosthesis comprising a substrate formed from a titanium alloy and a coating formed from a ceramic material comprising titanium ionically bonded to at least the non-articulating load bearing surface and the articulating load bearing surface of the orthopedic prosthesis to a thickness of 8–10 microns, whereby the ceramic coating defines a hardness greater than the substrate and substantially prevents abrasion of the substrate.

* * * * *